US009833395B2

(12) United States Patent
Koshti et al.

(10) Patent No.: US 9,833,395 B2
(45) Date of Patent: Dec. 5, 2017

(54) SUSTAINABLE COLD-DISPERSIBLE PEARLESCENT CONCENTRATE

(71) Applicant: GALAXY SURFACTANTS LTD., Pawne, Navi Mumbai, Maharashtra (IN)

(72) Inventors: Nirmal Koshti, Piscataway, NJ (US); Pritesh Rajaram Mhatre, Raigad (IN); MilindKumar Suresh Kalekar, Navi Mumbai (IN); Pooja Vaidya Kshirsagar, Nagpur (IN)

(73) Assignee: GALAXY SURFACTANTS LTD., Navi Mumbai, Maharashtra (IN)

( * ) Notice: Subject to any disclaimer, the term of this patent is extended or adjusted under 35 U.S.C. 154(b) by 139 days.

(21) Appl. No.: 14/916,814

(22) PCT Filed: Mar. 26, 2014

(86) PCT No.: PCT/IN2014/000193
§ 371 (c)(1),
(2) Date: Mar. 4, 2016

(87) PCT Pub. No.: WO2015/059711
PCT Pub. Date: Apr. 30, 2015

(65) Prior Publication Data
US 2016/0206537 A1 Jul. 21, 2016

(30) Foreign Application Priority Data
Oct. 25, 2013 (IN) .......................... 3368/MUM/2013

(51) Int. Cl.
| | | |
|---|---|---|
| *C11D 1/10* | (2006.01) | |
| *C11D 3/20* | (2006.01) | |
| *C11D 3/26* | (2006.01) | |
| *C11D 3/42* | (2006.01) | |
| *A61K 8/42* | (2006.01) | |
| *A61Q 5/02* | (2006.01) | |
| *A61K 8/34* | (2006.01) | |
| *A61K 8/37* | (2006.01) | |
| *A61K 8/44* | (2006.01) | |
| *A61K 8/46* | (2006.01) | |
| *A61Q 19/10* | (2006.01) | |
| *A61K 8/365* | (2006.01) | |

(52) U.S. Cl.
CPC .................. *A61K 8/42* (2013.01); *A61K 8/34* (2013.01); *A61K 8/365* (2013.01); *A61K 8/37* (2013.01); *A61K 8/375* (2013.01); *A61K 8/44* (2013.01); *A61K 8/466* (2013.01); *A61Q 5/02* (2013.01); *A61Q 19/10* (2013.01); *C11D 1/10* (2013.01); *A61K 2800/30* (2013.01); *A61K 2800/412* (2013.01); *A61K 2800/436* (2013.01); *A61K 2800/592* (2013.01); *A61K 2800/805* (2013.01)

(58) Field of Classification Search
CPC .. C11D 1/10; C11D 1/126; C11D 1/66; C11D 3/0089; C11D 3/2079; C11D 3/33; C11D 3/3463

USPC ....... 510/126, 127, 130, 136, 137, 138, 488, 510/499, 501
See application file for complete search history.

(56) References Cited

U.S. PATENT DOCUMENTS

| | | | |
|---|---|---|---|
| 2,729,657 A | 1/1956 | Krems | |
| 4,654,207 A * | 3/1987 | Preston | ............... A61K 8/37 510/119 |
| 4,777,038 A | 10/1988 | Scheuffgen | |
| 4,824,594 A | 4/1989 | Hoeffkes et al. | |
| 4,948,528 A | 8/1990 | Hoeffkes et al. | |
| 5,017,305 A | 5/1991 | Hoeffkes et al. | |
| 5,560,873 A * | 10/1996 | Chen | ................. A61K 8/39 510/120 |
| 5,711,899 A | 1/1998 | Kawa | |
| 6,147,124 A | 11/2000 | Ansmann et al. | |
| 6,165,955 A * | 12/2000 | Chen | ................. A61K 8/375 510/122 |
| 6,727,217 B1 * | 4/2004 | Nieendick | ............ C11D 3/0089 424/70.19 |
| 7,056,379 B2 * | 6/2006 | Nieendick | ............... A61K 8/375 106/502 |
| 7,217,752 B2 * | 5/2007 | Schmucker-Castner | ........... A61K 8/365 524/291 |
| 7,578,995 B2 | 8/2009 | Frantz | |
| 8,114,824 B1 | 2/2012 | Dasgupta et al. | |
| 8,263,538 B2 | 9/2012 | Tsaur et al. | |

(Continued)

FOREIGN PATENT DOCUMENTS

| | | |
|---|---|---|
| EP | 0983055 | 5/1999 |
| IN | 1669/MUM/2013 | 5/2013 |

OTHER PUBLICATIONS

Ananthapadmanabhan, et al., "A Novel Glycinate-based Body Wash", Journal of Clinical Aesthetic Dermatology 23-30 6(6) (2013).
BASF, "Safety Data Sheet", DIN safety data sheet Dimetnylaminopropylamine (DMAPA), 1989.
Bolzinger, et al., "Effects of surfactants on crystallization of ethylene glycol distearate in oil-in-water emulsion", Colloids and Surfaces A:Physiochem. Eng. Aspects, 93-100, 299 (2007).

(Continued)

*Primary Examiner* — Gregory R Delcotto
(74) *Attorney, Agent, or Firm* — Kramer Amado, P.C.

(57) ABSTRACT

Sustainable, free-flowing, cold-dispersible pearlescent concentrates are made without using any controversial or known toxic substance is disclosed herein. The pearlizing concentrates of the instant invention are free of alkyl sulphates/alkyl ether sulphates, alkanol amides, alkylamidopropyl betaines, and esters of ethylene glycol. The pearly concentrates of the present invention employ 'super-mild' surfactants to disperse vegetable plant derived 1,3-proane diol stearates. Also, these concentrates are preserved without any controversial antimicrobials such as parabens, isothiazolinones and formaldehyde releasers.

9 Claims, No Drawings

(56) References Cited

U.S. PATENT DOCUMENTS

| | | | |
|---|---|---|---|
| 8,268,767 B2 | 9/2012 | Tsaur et al. | |
| 2004/0086470 A1* | 5/2004 | Nieendick | A61K 8/06 424/63 |
| 2005/0172859 A1* | 8/2005 | Nieendick | A61K 8/375 106/502 |
| 2006/0079414 A1* | 4/2006 | Nieendick | A61K 8/375 510/119 |
| 2015/0335550 A1* | 11/2015 | Koshti | A61K 8/42 510/126 |

OTHER PUBLICATIONS

Boyxen, "Next Generation Euperlan PK4000. New Oleochemical Based Opacifier Lamesoft TM", Olaz, Szappan, Kosmetica, 50 evofolyam (2001).

Health, "Hazardous Substance Fact Sheet on Ethylene Glycol", NJ Department of Health, USA, Jul. 2012.

Orth, "Standardizing Preservative Efficacy Test Data", Cosmetics and Toiletries, Mar. 1991.

* cited by examiner

SUSTAINABLE COLD-DISPERSIBLE PEARLESCENT CONCENTRATE

FIELD OF INVENTION

The present invention relates to free-flowing, cold-dispersible, pearlescent concentrates for personal care and home care compositions. Particularly, these pearlescent concentrates are provided without involving harmful ingredients such as alkyl sulphates/alkyl ether sulphates, alkanol amides, alkylamidopropyl betaines and esters of ethylene glycol. More particularly, the present invention relates to pearlescent concentrates comprising mild surfactants such as glycinates and isethionates and pearlizing agent such as propane diol diesters. Further, the pearlescent concentrate is preserved without employing parabens, isothiazolinones or formaldehyde releasers.

BACKGROUND OF INVENTION

Personal care compositions such as face-washes, body-washes, hand-washes and shampoos etc. are made to look aesthetically attractive by incorporation of the pearlescent additives. These pearlescent additives impart iridescent sheen or glow to personal and home care formulations. The examples of commonly used pearlescent additives are monoesters or diesters of ethylene glycol (Formula I), propylene glycol, oligomeric alkylene glycols, glycerol esters of fatty acids, typically higher carbon chains with $C_{14}$ to $C_{22}$ and monoalkanol amides of fatty acids (Formula II);

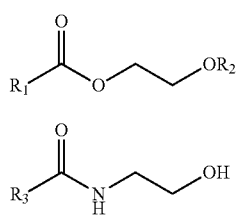

Formula I

Formula II in which $R_1$ denotes $C_{13}$ to $C_{21}$ alkyl group, $R_2$ is H or $R_1CO$ and $R_3$ is $C_8$ to $C_{22}$ alkyl group.

A typical procedure for converting the dull appearance of cosmetic formulations (face-wash, body-wash, shampoo and other aqueous compositions of surfactants) into a pearly (shiny) look involves addition of pearlescent additive (pearly wax) like distearate of ethylene glycol to the entire formulation and heating under agitation above the melting points of the pearlescent additives (70-80° C.) to ensure homogeneous mixture. This is then followed by cooling the entire mass gradually under slow agitation. This way, the pearly waxes are allowed to crystallize into platelet like structures so that the uniformly dispersed platelets reflect light imparting the shine to the products.

Developing right size and shape of pearly wax is a kind of complex technology (Norbert Boyxen in Olaz, Szappan, Kosmetica, 50 evofolyam (2001) and M. A. Bolzinger et al., Colloids and Surfaces A: Physiochem. Eng. Aspects, 93-100, 299 (2007) and getting the consistency in pearly sheen of the finished personal care products, batches after batches, is not always easy. This problem has been addressed by the 'easy-to-use' cold-dispersible pearlescent concentrates.

The surfactants manufacturing industry developed the technology to manufacture so called 'cold-dispersible', 'free-flowing' pearlescent concentrates for the ease of incorporation of pearly waxes into personal and home care formulations (U.S. Pat. Nos. 4,777,038, 4,824,594, 4,948, 528 & 5,017,305). These 'cold-dispersible pearlescent concentrates' are nothing but pearl waxes dispersed in the crystal form in aqueous surfactant systems. These are very stable and concentrated, yet flowable, dispersions, that are required to be added anywhere between 0.5 to 5.0% to the personal or home care compositions to impart the pearlescent appearance. This operation is done with simple mixing without heating and hence these are referred to as 'cold-dispersible' (cold-processable) pearlescent concentrates. In addition to the benefits of ease of incorporation and saving of energy, the other significant advantage that is derived from these concentrates is that of the consistency in the pearlescent appearance in the final personal and home care compositions. Several cold pearlescent concentrates are available commercially, for example, Sparkle series from Galaxy Surfactants Ltd, Mirasheen series from Rhodia (Solvay), Euperlan PK series from Cognis (BASF), Zohar-pearl series from Zohar Dalia and Quickpearl series from Lubrizol (Table I).

TABLE I

| Manufacturer | Trade name | Ingredients |
|---|---|---|
| Rhodia-Solvay | Mirasheen CP 920 | Ethylene glycol distearate, Laureth-7, Coamidopropyl betaine, Sodium cocoamphoacetate, Sodium laureth sulfate, DMDM Hydantoin |
| Rhodia-Solvay | Mirasheen STAR K | Ethylene glycol distearate Sod laureth sulphate, Cocoamidopropyl betaine |
| Cognis-BASF | EUPERLAN PK 1200 | Ethylene glycol distearate Coco-glucoside, |
| Cognis-BASF | EUPERLAN PK 4000 | Ethylene glycol distearate, Laureth-4, Cocamidopropyl betaine |
| Cognis-BASF | EUPERLAN PK 710 BENZ | Ethylene glycol distearate Sodium laureth sulfate, Cocamide MEA, |
| Cognis-BASF | EUPERLAN PK 710 | Ethylene glycol distearate Sodium laureth sulfate, Cocamide MEA |
| Cognis-BASF | EUPERLAN PK 771 | Ethylene glycol distearate, Sodium laureth sulfate, Cocamide MEA, Laureth-10 |
| Cognis-BASF | EUPERLAN PK 771 BENZ | Ethylene glycol distearate, Sodium laureth sulfate, Cocamide MEA, Laureth-10 |
| Cognis-BASF | EUPERLAN PK 810 | Ethylene glycol distearate, Sodium laureth sulfate, Cocamide MEA, Laureth-10 |
| Cognis-BASF | EUPERLAN PK 900 BENZ-W | PEG-3 stearate, Sodium laureth sulfate |
| Lubrizol | Quickpearl ™ 810 | Ethylene glycol distearate, Sodium laureth sulfate, Cocamide MEA, Laureth-10 |
| Lubrizol | Quickpearl ™ I | Ethylene glycol distearate, Sodium lauryl sulfate |
| Lubrizol | Quickpearl ™ II | Ethylene glycol distearate Sod laureth sulphate |
| Lubrizol | Quickpearl ™ PK3 Pearlizing Agent | Ethylene glycol distearate, Laureth-4, Cocamidopropyl betaine |
| Galaxy Surfactants Ltd | Sparkle 660 | Ethylene glycol distearate, Sodium laureth sulfate |

Typically, all cold-dispersible pearlescent concentrates (TABLE I) are made of three components a) pearly waxes b) surfactants and c) water. Waxes are emulsified with surfactants in aqueous medium and then are gradually allowed to crystallize in the surfactant environment. This process results in a stable uniform dispersion of platelet like structures that reflect light. The examples of waxes are glycol esters of stearic acid or other fatty esters (Formula I) and alkanolamides (Formula II). The surfactants that are used to disperse the pearly waxes are from all categories, namely, anionic, cationic, amphoteric, zwitterionic and non-ionic (U.S. Pat. Nos. 5,560,873, 5,711,899, 6,147,124, & 7,578, 995).

A quick look at commercial products and the patented literature reveals that the most commonly used ingredients for free-flowing cold-dispersible pearlescent concentrates are 1) ethylene glycol stearates 2) alkanolamides 3) sodium laureth sulphate (anionic surfactant) 4) cocoamido propyl betaine (zwitterionic surfactant) 5) ethylene oxide adducts of fatty alcohols (non-ionic surfactant) and preservatives (TABLE I).

Alkanolamides are synthesized by reacting fatty acids or their esters with monoethanol amine or diethanol amine to give corresponding alkyl monoethanolamides or alkyl diethanol amides. The alkanol amides, particularly, alkyl diethanol amides have been reported to generate carcinogenic nitrosoamines (U.S. Pat. No. 5,560,873) due to residual free diethanol amine. For example, cocodiethanol amide (Cocamide DEA) has significant amount of residual diethanol amine that can generate the carcinogenic nitrosoamine after coming in contact with other personal care ingredient that are capable of nitrosating the secondary amine. Cocamide DEA has been listed as cancer causing substance by the Office of Environmental Health Hazard Assessment of California state government, USA (California prop 65 list). Personal care formulators have become very wary of using Cocamide MEA (cocomonoethanol amide) since monoethanol amine used in the manufacture can have diethanol amine as an impurity since there is no way of synthesizing monoethanol amine exclusively and selectively without generation of diethanol amine.

Alkyl sulphates and alkyl ether sulphates are known for being harsh on both skin and hair. In fact sodium lauryl sulphate is taken as a standard irritant for irritancy measurement. Sodium lauryl ether sulphate (SLES) is made by sulphating ethoxylated lauryl alcohol of varying degree of ethylene oxide (0.5 to 3.0 moles of EO per one mole of fatty alcohol). Any grade of SLES that is available in the market contains significant amount of sodium lauryl sulphate (more than 20%) that is an established irritant to human skin and mucosa. In the class of anionic surfactants 'sulphates' in general are known to be the highest irritants compared to 'sulphonates or sulphosuccinates'. While doing the cleansing job, alkyl ether sulphates strip away proteins and lipids of cuticle of hair and stratum corneum of skin. Skin's moisture regulation mechanism is seriously affected due to adverse action of harsh surfactants on the proteins and lipids of upper layers of stratum corneum. Products 'without sulphates' have been launched that do less or no damage to hair. An example of this is L'Oreal's 'sulphate-free' 'Everpure' range of shampoos. Unilever's Dove range of body washes uses mild surfactants like cocoyl isethionate and sodium glycinate to reduce damaging effect of harsh surfactants like fatty alchohol ether sulphates (Nutrium technology, A novel glycinate-based body wash, K. P. Ananthapadmanabhan et al., Journal of Clinical Aesthetic Dermatology 23-30, 6(6), 2013).

Ethylene glycol stearates, mono or di, are the main pearlizing waxes that are used in these concentrates and these are by far the largest active component in the cold-dispersible, free-flowing pearlescent concentrates that are either available commercially or reported in literature. This is because these are the substances that crystallize and impart pearly effect to the final composition. Ethylene glycol stearates are made by esterifying stearic/palmitic acids with ethylene glycol. Though fatty acids are largely obtained from vegetable oils, mainly palm and coconut oil, ethylene glycol (mono ethylene glycol, MEG) has its origin in a petrochemical, ethylene oxide. Besides MEG's petrochemical origin, the more worrisome fact is its toxicity. The major impurity, diethylene glycol (DEG) in MEG is a serious concern. Ethylene glycol is listed by American Association of Poison Control Center that keeps track of fatalities due to ethylene glycol. Ethylene glycol is a teratogen in animals and hence suspected to be teratogen in human being. (Hazardous Substance Fact Sheet on Ethylene Glycol, New Jersey Department of Health, USA. Monoethylene glycol is on the Special Health Hazard Substance List) This means it is a huge concern for the environment and the ecology. All personal care and home care products like body-washes and hand-washes go to environment after the usage and are biodegraded to give ethylene glycol from the corresponding pearly distearates. The impurity, diethylene glycol (DEG) in mono ethylene glycol is another poison. US code of federal regulations allow no more than 0.2% of DEG in polyethylene glycols used as food/drug or toothpaste additive. DEG is well-known poison and epidemiology is full of records of human deaths. In summary, in addition to being a petrochemical derived glycol, MEG is quite toxic due to impurities like DEG and by itself MEG is a danger to the environment due to its teratogenicity. There has been one commercial product by Cognis-BASF (Care chemicals division, Technical Data Sheet, EUPERLAN® GREEN) by the trade name Euperlan Green seems to be the only example wherein ethylene glycol stearate has been replaced by stearyl citrate and the non-ionic surfactant of lauryl glucoside is used to disperse the pearly wax. This was done with the intention of avoiding ethylene oxide (EO) based products.

Cocoamidopropyl betaine, CAPB is popular zwitterionic surfactant and very commonly used in pearlescent concentrates. It is manufactured from methyl ester of fatty acid or from fatty acids by reacting with N,N-dimethyl propyl diamine to get the corresponding amido amine that is subsequently quaternized by monochloroacetic acid into final zwitterionic surfactant. Though it is one of the most economical zwitterionic surfactant it is impossible to manufacture CAPB that would be totally devoid of traces of free N,N-dimethyl propyl diamine and monochloroacetic acid. Both starting materials that are used in the manufacture of CAPB are quite toxic (DIN safety data sheet on N,N-dimethyl propyl diamine, BASF, 1989). N,N-dimethyl propyl diamine is a skin-corrosive (Category 1B) and skin sensitizing (Category The other trace level impurity in CAPB is highly acidic and corrosive monochloro acetic acid, having $LD_{50}$ 76 mg/kg, which is reported to penetrate through skin and mucous membrane.

A survey of commercially available cold pearlescent concentrates reveals that use of parabens, formaldehyde releasers and isothiazolinones. To move away from the controversial substances some manufacturers adopted different strategy of maintaining the acidic pH and with acids as preservatives.

In some marketed pearly concentrates very acidic pH is maintained and the same are preserved with acids like benzoic acid or formic acid. For example Euperlan 771 is preserved with benzoic acid. Euperlan PK4000, Euperlan PK810 are preserved with formic acid. Similarly, MackPearl TTE and MacPearl SSO special are preserved with formic acid. Euperlan Green is preserved by maintaining very acidic pH of 3 to 4. Euperlan PK771 and Mirasheen Star K and Mirasheen Star NB are preserved with isothiazolinones. Mirasheen CP 820/G and Mirasheen A-220 are preserved with DMDM hydantoin.

It should be noted that these pearlescent concentrates are for personal care products and formic acid should not be used as preservative for end personal care formulation as it keeps the pH so acidic. Moreover, formic acid is corrosive to skin and is very reactive molecule and can react with a variety of functionality of other ingredients.

Methyl and chloro analogs of Isothiazolinone (commercial trade name Kathon CG by Rohm and Haas) are quite toxic and hence they are allowed at a few ppm levels and only in rinse-off products. They are not used in any leave-on products. Japan's regulatory body does not permit the usage of these Isothiazolinones analogs. DMDM hydantoin, another antimicrobial, prevalent in some of the pearlescent concentrates, is a well-known formaldehyde releaser.

In view of this prevalent use of these established toxic antimicrobials (parabens, isothiazolinones, formaldehyde releasers, halogenated compounds, phenolic molecules) it is very essential to preserve these pearlescent concentrates with something very effective but at the same time safe and eco-friendly.

U.S. Pat. No. 5,560,873 discloses pearlizing concentrates that address the above mentioned issues to some extent. It teaches use of mild surfactants like sodium cocoyl isethionate and sodium cocoyl N-methyl taurate in place of the harsh alkyl ether sulphates. The pearlescent blends of this patent are expected to be mild on skin since they do not contain fatty alcohol ether sulphates. However, this patent does not report or refer to any literature or include data to suggest any synergy in terms of mildness arising out of in any particular combination of O-acyl isethionate and N-acyl taurate.

It also teaches creating pearlescent concentrates without carcinogenic alkanolamides, which can be used in personal care compositions. However, the examples cited in this patent employ ethylene glycol monostearate as the pearly wax, and cocoamidopropyl betaine, zwitterionic surfactant. Also, the preservatives listed in this patent application are the most controversial antimicrobials, the parabens and the formaldehyde releasers like imidazolidinyl urea. Parabens have been reported to have endocrine disrupting estrogenic activity and some deleterious effect on reproductive system. Formaldehyde is classified as category 3 CMR (carcinogenic, mutagenic and reproductive toxic). Also, released formaldehyde is a very reactive chemical (aldehyde functionality) capable of reacting with several personal care ingredients.

Euperlan Green that obviates first four ingredients listed above, however, uses extreme acidity for the preservation purpose. This extreme acidity comes from significant level of free acid. Also, the constituent members of Euperlan Green have significant characteristic odor.

Personal cleansing compositions of today have undergone revolutionary change. Recently, Tsaur et al. have revolutionized cleansing technology by inventing various combinations of mild surfactants. Synergistic combinations of O-acyl isethionate and N-acyl glycinate/sarcosinate as 'super mild' surfactants are reported in the recent literature (U.S. Pat. Nos. 8,268,767, 8,263,538, 8,114,824).

U.S. Pat. No. 8,263,538 teaches a combination of N-acyl amino acid surfactants, such as sodium N-cocoyl glycinates and sodium N-cocoyl sarcosinates, with amphoteric/zwitterionic surfactants for 'super mild' personal cleansing compositions that showed total irritation score using patch test methodology to be less than 75% relative to 0.5% aqueous sodium dodecyl sulphate solution.

Yet another recent patent by the same group (Tsaur et al. U.S. Pat. No. 8,268,767) reports combinations of cleansing surfactants that not only cleanse, moisturize and deliver the benefit agents but are 'super mild' to skin. The said compositions comprise of both O-acyl isethionates (Formula III, $R_4=C_7$ to $C_{21}$, $R_5=H$, methyl and M is a cation selected from $Na^+$, $K^+$, $NH_4^+$) and N-acyl amino acid surfactants (Formula IV, $R_4=C_7$ to $C_{21}$, $R_5=H$, methyl, M is a cation selected from $NH_4^+$, $Na^+$ or $K^+$) for liquid cleansers for both skin and hair.

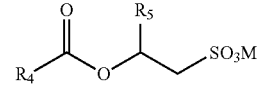
Formula III

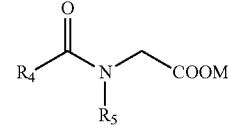
Formula IV

The compositions are said to be 'super-mild' to skin when tested by standard patch test (in-vivo) method on human volunteers. The above mentioned patent also reveals exceptionally mild compositions that deliver the occlusive moisturizers very effectively. Similarly, U.S. Pat. No. 8,114,824 discloses compositions with O-acyl isethionates and N-acyl amino acid surfactants that could accommodate maximum amount of moisturizer. In summary, the surfactant systems comprising of O-acyl isethionates and N-acyl amino acid surfactants as main ingredients have been reported to be very good cleansing systems that are 'super mild/gentle' on skin and excellent delivery vehicles for actives (benefit agents like emollients, silicones, triglycerides and petrolatum). The above mentioned patent teaches that the 'super mildness' and 'delivery benefits' are obtained due to the exceptional synergy exhibited by the combination of these two classes of mild surfactants, namely, O-acyl isethionates (Formula III) and N-acyl amino acid surfactants (Formula IV).

The commercial products using the 'super-mild' surfactant combinations (K. P. Ananthapadmanabhan et al., Journal of Clinical Aesthetic Dermatology 23-30, 6(6), 2013) are being made (Dove body wash, Nutrium Moisture™ technology by Unilever, Fine Fairness Cleanser by Johnson and Johnson).

Today's consumer and the manufacturers of personal care products are conscious about the deleterious effects of chemicals that are used in formulations. Conscious efforts are being made to use the safest ingredients that are also eco-friendly and sustainable. Personal care formulators are formulating cleansing systems with 'super-mild' surfactants (for cleansing face, body and hair). Consciously, toxic ingredients are being avoided and this includes the antimicrobial preservatives. The adjectives like 'sulphate-free', 'paraben free' and 'alkanolamide free' are getting popular. Certainly, to improve the aesthetics of such carefully formulated products, the formulators need a cold-dispersible pearlizing concentrate that is not just made from safe and non-toxic substances but it should be completely eco-friendly and sustainable. Currently, no such cold-dispersible pearlizing concentrate is available.

Thus, there is need for a cold-dispersible pearlescent concentrate that would be devoid of all controversial substances including 1) harsh surfactants like alkyl sulphates/ alkyl ether sulphates 2) alkanol amides based on monoethanol amine and diethanol amine 3) pearly waxes based on ethylene glycol 4) amidobetaines and 5) preservatives systems containing parabens, formaldehyde releasers, and isothiazolinones.

OBJECTS OF INVENTION

Accordingly, it is, an objective of the present invention to develop a cold-dispersible pearlescent concentrates which is devoid of all controversial ingredients such as harsh surfactants, carcinogenic alkanol amides, eco-toxic pearly waxes, amidobetaines and antimicrobials.

It is another objective of the present invention to develop a cold-dispersible pearlescent concentrate that is based on mild, non-toxic and eco-friendly ingredients such as 'mild surfactants and fatty acid esters of 1,3-propane diol as pearl wax.

It is a further object of the present invention to develop a process for manufacturing cold-dispersible pearlescent concentrate.

SUMMARY OF INVENTION

In accordance with the above objectives, the present invention provides aqueous, free flowing cold-dispersible pearlescent concentrates, which comprises;
1) Combination of 'super-mild' surfactants;
2) Esters of 1,3-propane diol as pearl wax;
3) N-acyl glycines; and
4) Preservative system comprising phenoxy ethanol, capryloyl glycine and undecylenoyl glycine.

Thus, the present invention discloses free-flowing, aqueous cold-dispersible pearlizing concentrates that are made by avoiding all controversial ingredients such as harsh surfactants, carcinogenic alkanol amides, non-ecofriendly pearly waxes, amidobetaines and antimicrobials.

The cold-dispersible, aqueous pearlescent concentrates of the present invention comprises
a) 10 to 20% by weight of mild surfactants selected from O-acyl isethionates (Formula III) and N-acyl amino acid surfactants (Formula IV)

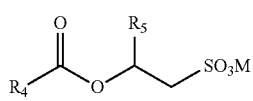

Formula III

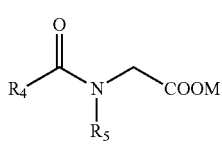

Formula IV wherein, $R_4$ is selected from $C_7$ to $C_{21}$ saturated or unsaturated alkyl group, $R_5$ is H or methyl and M is a cation selected from $Na^+$, $K^+$, $NH_4^+$;

b) 15 to 30% by weight of pearlizing wax selected from 1,3-propane diol esters of fatty acids (Formula V);

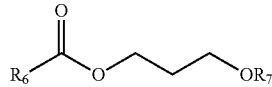

Formula V wherein, $R_6$ is selected from $C_{13}$ to $C_{21}$ saturated or unsaturated alkyl group, $R_7$ is H or $R_6CO$;
c) 2 to 6% by weight of N-acyl glycine Formula VI;

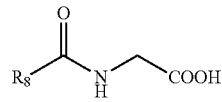

Formula VI wherein, $R_8$ is selected from $C_7$ to $C_{21}$ saturated or unsaturated alkyl group; and
d) 0.8 to 1.2% by weight of preservative system consisting of phenoxy ethanol, capryloyl glycine and undecylenoyl glycine.

All percentages and ratios herein are on weight percent basis unless otherwise stated. The term 'super-mild' surfactants herein refer to O-acyl isethionates and N-acyl amino acid surfactants and their combination thereof.

The term 'cold' as utilized herein refers to the ability of the concentrate to be added without heating the personal and home care products.

In the second aspect, the present invention is directed to personal care compositions containing the cold-dispersible pearlizer concentrate of the present invention.

DETAILED DESCRIPTION OF INVENTION

The present invention relates to a cold-dispersible pearlescent concentrate that is composed of safe, mild, non-toxic and eco-friendly ingredients. The pearlescent compositions of the patent application are based on established 'super-mild' and completely biodegradable surfactants system, the combination of O-acyl isethionates (Formula III) and N-acyl amino acid surfactants (Formula IV), eco-friendly pearly wax made from vegetable oil derived fatty acids and corn derived 1,3-propane diol, and non-toxic, non-controversial preservatives.

In the first aspect, the present invention is directed to aqueous, cold-dispersible pearlescent concentrates, which comprises;
1) Combination of 'super-mild' surfactants;
2) Esters of 1,3-propane diol as pearl wax;
3) N-acyl glycines; and
4) Preservative system comprising phenoxy ethanol, capryloyl glycine and undecylenoyl glycine.

The present invention discloses free flowing, aqueous, cold-dispersible pearlizing concentrates that are made by avoiding all controversial ingredients such as harsh surfactants, carcinogenic alkanol amides, non-ecofriendly pearly waxes, amidobeatines and antimicrobials.

The aqueous pearlescent concentrates of the present invention comprise of
a) 10 to 20% by weight of mild surfactants selected from O-acyl isethionates (Formula III) and N-acyl amino acid surfactants (Formula IV);

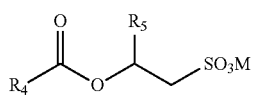

Formula III

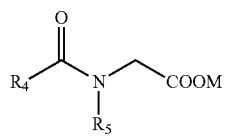

Formula IV wherein, $R_4$ is selected from $C_7$ to $C_{21}$ saturated or unsaturated alkyl group, $R_5$ is H or methyl and M is a cation selected from $Na^+$, $K^+$, $NH_4^+$;

b) 15 to 30% by weight of pearlizing wax selected from 1,3 propane diol esters of fatty acids (Formula V);

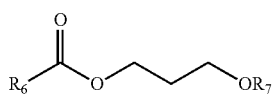

Formula V wherein, $R_6$ is selected from $C_{13}$ to $C_{21}$ saturated or unsaturated alkyl group, $R_7$ is H or $R_6CO$;

c) 2 to 6% by weight of N-acyl glycine (Formula VI)

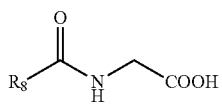

Formula VI wherein, $R_8$ is selected from $C_7$ to $C_{21}$ saturated or unsaturated alkyl group; and d) 0.8 to 1.2% by weight of preservative system consisting of phenoxy ethanol, capryloyl glycine and undecylenoyl glycine.

In another aspect, the present invention is directed to personal care compositions containing the cold-dispersible pearlizer concentrate of the present invention. Accordingly, the invention provides personal care compositions comprising about 2 to 10% by weight of aqueous, cold-dispersible, cold processable pearlescent concentrates of the instant invention.

In the present invention, the aqueous, cold-pearlizing concentrate is prepared by emulsifying the pearlizing wax by a combination of mild surfactants that have been established as 'super-mild' surfactants. The cold-dispersible pearlescent concentrates of the present invention are made by dispersing pearly wax, stearates of 1,3-propane diol (Formula V) using 10 to 20% by weight of mild surfactants selected from O-acyl isethionates (Formula III) and N-acyl amino acid surfactants (Formula IV, $R_4=C_7$ to $C_{21}$, $R_5=H$, methyl, M is a cation selected from $NH_4^+$, $Na^+$ or $K^+$).

In a preferred embodiment, the ratio of O-acyl isethionates and N-acyl amino acid surfactants is from 2.0:0.5 to 0.5:2.0.

O-Acyl isethionates (Formula III) can be selected from sodium cocoyl isethionate or sodium lauroyl isethionate. Commercially, the isethionates are available in solid form (powder, needles or granules) with a minimum 80% anionic active matter. N-acyl amino acid surfactants (Formula IV) can be selected from sodium lauroyl glycinate, sodium cocoyl glycinate, sodium lauroyl sarcosinate or sodium cocoyl sarcosinate, which are available as aqueous solutions or in powder form. The preferred blends of 'super-mild' surfactants are O-acyl isethionates and N-acyl glycinates and the most preferred combination of super-mild surfactants is sodium N-cocoyl glycinate and sodium O-cocoyl isethionate in the ratio of 2:1. The blend of O-acyl isethionates and N-acyl glycinates used in the present invention are prepared by the process reported in Indian Patent Application number 1669/MUM/2013/by Koshti et al.

The pearlizing wax of this patent application is selected from mono or di ester of 1,3-propane diol and fatty acids (Formula V). The alkyl chain can be selected from $C_{12}$ to $C_{22}$ for either mono or disters of propane diol. The preferred pearly wax of the instant invention is diester of fatty acids and most preferred wax is 1,3-proane diol distearate (CAS No 75537-28-9). The fatty acids needed for preparing the esters are derived from vegetable oils like coconut oil or palm kernel oil. The vegetable oils with higher degree of unsaturation can be hydrogenated so that unsaturated alkyl chains of oleic, linoleic and linolenic or erucic acids can be converted to the corresponding saturated analogs of stearic acid or behenic acid. The stearic acid that is used for the preparation of distearates of 1,3-propane diol is procured from commercially available grades that are mixtures of stearic and palmitic acid, with stearic content being 40 to 80%. Pure palmitic or stearic acid can also be used to make the pearly waxes. 1,3-Propane diol is made by fermentation of corn syrup. 1,3-Propane diol made from renewable vegetable source is commercially available under the trade name of Zemea® propane diol (CAS 504-63-2) offered by DuPont-Tate & Lyle. This diol, a personal care ingredient, is completely non-toxic and is used as humectants. Thus, the diesters of 1,3-propane diol, the pearly waxes of the present invention are completely biodegradable and their degradation products, namely, fatty acids and propane diol, are completely eco-friendly unlike ethylene glycol of glycol stearates.

The non-ionic surfactant, employed in the pearlescent concentrates of the present invention is N-acyl glycine (Formula VI). This surfactant in its acid form is made by acidifying the aqueous solutions of commercially available sodium N-acyl glycinates and phase separating the N-acyl glycine (the acid form, forms upper layer) from the aqueous acidic layer. The N-acyl glycines can be further washed with water in hot condition to remove the mineral acidity. Depending upon the length of the alkyl chain on nitrogen, N-acyl glycine can be a liquid or a solid. In the examples of the instant invention, N-cocoyl glycine with alkyl chain distribution of $C_8$ to $C_{16}$ was predominantly used. It is the same alkyl chain distribution of sodium cocoyl glycinate (CAS No. 90387-74-9). N-acyl sarcosines made in similar way can also be used in place of N-acyl glycine (U.S. Pat. No. 2,729,657).

In a preferred embodiment, 2-6% N-acyl glycine is used, preferably 4-6%.

The cocoyl cut alkyl chain distribution for N-cocoyl glycinate and N-cocoyl glycine is given in TABLE II

TABLE II

| Carbon chain distribution of Cocoyl group | |
|---|---|
| Carbon chain | Range |
| $C_8$ | 4-12% |
| $C_{10}$ | 4-14% |

TABLE II-continued

Carbon chain distribution of Cocoyl group

| Carbon chain | Range |
|---|---|
| $C_{12}$ | 59-65% |
| $C_{14}$ | 14-24% |
| $C_{16}$ | 1-8% |
| $C_{18}$ | 0.5 to 12% |

It is obvious to those with ordinary skilled in the art that alkyl group $R_8$ is selected from one alkyl chain or mixture of alkyl chains and can be selected from carbon atoms ranging from $C_8$ to $C_{20}$.

The pearlescent concentrates of the present application are preserved by a three component blend which is a mixture of three components, namely, phenoxy ethanol (CAS No 122-9-6, EC No: 204-589-7), capryloyl glycine (CAS No14246-53-8) and undecylenoyl glycine (CAS No 54301-26-7, EINECS No 427-430-5) in the ratio of 8:1:1 by weight.

Capryloyl glycine, also known as N-octanoyl glycine, is a well-known skin purifier/protector. Commercially, it is available as Lipacide C8G from SEPPIC, France. It is active against most of the natural resident micro-flora that reside on human skin and is used in anti-acne, antiperspirant and deodorant preparations.

Undecylenoyl glycine is reported to possess anti-acne and anti-dandruff activity (EP 0983055131). It is commercially available as Lipacide UG and is used as dermopurifier.

2-Phenoxy ethanol occurs in nature (Chinese Green Tea) and has been consumed by human race for centuries. It is a gentle antimicrobial and is preferred in preserving vaccines that contain very labile proteins. 2-Phenoxy ethanol is active against Gram negative bacteria (Cosmetic and Drug Preservation, Principles and Practice, Vol I, Ed Jon Kabara, Marcel Dekker).

The preservative blend comprising 2-phenoxy ethanol, N-octanoyl glycine and N-undecylenoyl glycine in the ratio of 8:1:1 has been used at 1.2% level in Examples 1, 2 & 3 and 1% in shampoo, body wash and face-wash formulations of Examples 4, 5 and 6.

These preserved pearlescent concentrates from Examples 1, 2 and 3 have been challenge-tested using microorganisms with initial levels of inoculation of $10^8$ to $10^{10}$ cfu/ml as per CTFA guideline (Evaluation of preservatives to protect cosmetics' by D. Orth in Cosmetics and Toiletries, March 91).

As per CTFA guideline, on completing 28 days period of incubation, the concentrated blends of Example 1, 2 and 3 passed the challenge test. The test organisms that have been used in challenge test are *Pseudomonas aeruginosa, Staphylococcus aureus, Escherichia coli, Candida albicans* and *Aspergillus niger*. Thus, the preservative combination used in pearlescent concentrates of the present invention are made up of very 'safe and non-toxic' personal care ingredients and are free from parabens, formaldehyde donors, phenolic compounds, halogenated molecules and quaternary ammonium molecules.

In another embodiment, the invention provides a process for manufacture of cold-dispersible pearlescent concentrate which comprises;
1) Emulsifying pearly wax using combination of mild surfactants in a specified ratio that are established as 'super-mild' surfactants and a non-ionic surfactant in water at 75 to 80° C.;
2) Cooling the emulsified mass gradually to 45° C. over 2 to 4 hours under gentle agitation with the addition of antimicrobial preservatives and maintaining the whole mass at the same temperature for 12 to 24 hours followed by cooling to room temperature and
3) Adjusting the pH to 6.5 to 7.5 (if necessary) with citric acid followed by adjusting the desired solids content of the pearly concentrate. (Example 1, 2 and 3).

The pearly wax of used in the instant invention is a stearate ester of 1,3-propane diol and the non-ionic surfactant is N-acyl glycine.

The viscosity of the pearlescent blends thus obtained ranges between 3,000 to 20,000 cps and the solids content is kept minimum 35% by weight. The particle size distribution is between 5 to 15 □m ($D_{50}$) when measured using Malvern particle size analyzer (Mastersizer 2000E).

The pearlescent concentrate thus prepared can be stored at a temperature of from about 20° C. to about 40° C. for six months without any significant change in physical properties.

The aqueous, cold-dispersible pearlescent concentrates of the present invention can be specifically formulated into a wide variety of personal care and home care products. These products can be formulated by one skilled in the art utilizing conventional methods of preparation. The pearlizing concentrate of the instant invention imparts a high luster, nacreous look to body-wash, face-wash and shampoo (Example 4, 5 and 6). Generally, the personal or home care products can be made by merely mixing the personal or home care products together with the concentrate at room temperature.

Advantages of the Invention

1) The pearlescent concentrates of the instant invention are based on established 'super-mild' surfactants combination of O-acyl isethionates, N-acyl amino acid surfactants, particularly, glycinates (K. P. Ananthapadmanabhan et al., Journal of Clinical Aesthetic Dermatology 23-30, 6(6)).

2) These compositions are free from fatty alcohol ether sulphates (SLES) and hence mild on skin; avoids damage to hair cuticle and also devoid of cancer causing 1,4-dioxane.

3) The cold-dispersible pearlescent concentrates of the present invention use stearate esters of 1,3-propane diol. 1,3-Propane diol, unlike ethylene glycol (MEG is derived from petrochemical and is eco-toxic, proven teratogen in animals and possible teratogen for human. The impurity, DEG that can be present in MEG is highly poisonous) is derived from corn syrup by fermentation technology. Thus, 1,3-propane diol derived from renewable source is non-toxic substance and is used as humectant by cosmetic formulators.

4) The cold-dispersible pearlescent concentrates of the present invention do not use any controversial ingredient like alkanol amides, ethylene glycol based esters and alkyl amido propyl betaines.

5) The cold-dispersible pearlescent concentrates of the present invention avoids usage of controversial, estrogeinic, carcinogenic, incompatible antimicrobials e.g. parabens or formaldehyde releasers, phenolic, halogenated and quaternary ammonium type of molecules.

6) The pearlescent concentrates of the instant invention are preserved with a blend of phenoxy ethanol, capryloyl glycine and undecylenoyl glycine; all are established, commercially available and approved personal care ingredients.

7) The ingredients of the pearlescent concentrates of the instant invention make the final compositions, cold-processable, mild on skin, completely safe (toxicologically), and finally eco-friendly compared to what is available in market currently. This makes the compositions of the patent application completely sustainable from every aspect.

EXAMPLES

The present invention is now described by way of working non limiting illustrative examples. The detail of the invention provided in the following examples is given by the way of illustration only and should not be construed to limit the scope of the present invention.

Fatty acid, stearic acid was sourced from Palm Oleo SDN BHD, Malaysia. Biobased Zemea propane diol was sourced from DuPont Tate & Lyle Bio-Products, Loudon, USA. Preservative blend was available with Galaxy Surfactants Ltd, Navi Mumbai, India, under the trade name of Galguard NK4 which is a combination of 2-phenoxy ethanol, capryloyl glycine and undecylenoyl glycine in the ratio of 8:1:1 by weight.

Preparation of 1,3-propane diol distearate

The pearly wax 1,3-propane diol distearate was prepared by reacting two gmol of stearic acid and one gmol of 1,3-propane diol under the catalytic influence of sulphonic acid catalyst (0.02 mole %) at 130-140° C. The water of esterification was removed continuously with a steady purging of nitrogen throughout the progress of reaction. The reaction was monitored on the basis of acid value of the reaction mass and was continued till the acid value of <10 was attained. The product was obtained as white flakes, with saponification value of 195 and melting point of 52-57° C.

Preparation of cocoyl glycine

Cocoyl glycine was prepared from sodium cocoyl glycinate sourced from Galaxy Surfactants Ltd, Navi Mumbai. It is available with a trade name of Galsoft SCG. The 30% aqueous solution of sodium cocoyl glycinate is acidified with 10% sulphuric acid. After attaining the pH of 1.0, the separated solid, cocoyl glycine was filtered and washed with cold water to get rid of the acidity of mineral acid. It was dried and then used for creating the cold pearlescent concentrates (Examples 1, 2 and 3) of the present invention.

Example 1

Preparation of Cold-Dispersible Pearlizing Blend Using 'Super-Mild' Surfactants in 2:1 Ratio:Sodium Cocoyl Glycinate:Sodium Cocoyl Isethionate 2:1 and 1,3-Propane Diol Distearate

| Ingredients | Qty (g) |
|---|---|
| Sodium cocoyl glycinate (30% aq. solution) | 352 |
| Sodium cocoyl isethionate (85% active) | 56 |
| Cocoyl glycine | 60 |
| 1,3-Propane diol distearate | 200 |
| Water | 315 |
| Citric acid | pH adjustment (6-7) |
| Preservative:Galgurad NK 4 | 12 |
| (2-phenoxy ethanol, capryloyl glycine and undecylenoyl glycine in the ratio of (8:1:1) | |
| Weight of total batch | 1000 |

To a stirred solution of sodium cocoyl glycinate (352 g of 30% aqueous solution, 24% active with 5% sodium chloride) and sodium cocoyl isethionate (56 g, 85% active) in water (237 mL), was added cocoyl glycine (60 g) and the resulting mixture was heated to 80° C. for 15 minutes. To this mixture at 80° C., 1, 3-propane diol distearate (200 g) was added and stirred for additional 30 minutes. The resultant emulsion was then slowly cooled to 45° C. over two hours with gentle stirring. To this dispersion, water (78 mL) was added and mass was cooled to room temperature under gentle stirring over a period of two hours. pH was adjusted to 6 to 7 using citric acid. It was preserved with a 1.2% blend comprising 2-phenoxy ethanol, capryloyl glycine and undecylenoyl glycine in the ratio of (8:1:1)

Analysis:

Solids content: 42.7%

Viscosity at 25° C. Brookfield LV 4, rpm 12: 13000 cps pH (10% dispersion): 6.4

Sodium chloride content: 2%

Example 2

Preparation of Pearlizing Blend Using 'Super-Mild' Surfactants in 2:1 Ratio: Sodium Cocoyl Sarcosinate:Sodium Cocoyl Isethionate: 2:1 and 1,3-Propane Diol Distearate

| Ingredients | Qty (g) |
|---|---|
| Sodium cocoyl sarcosinate (30% aq. Solution, 24% active) | 352 |
| Sodium cocoyl isethionate 85% | 56 |
| Cocoyl glycine | 60 |
| 1,3-Propane diol distearate | 200 |
| Water | 315 |
| Citric acid | pH adjustment (6-7) |
| Preservative:Galgurad NK 4 | 12 |
| (2-phenoxy ethanol, capryloyl glycine and undecylenoyl glycine in the ratio of (8:1:1) | |
| Weight of total batch | 1000 |

To a stirred solution of sodium cocoyl sarcosinate (352 g of 30% aqueous solution, 24% active with 5% sodium chloride) and sodium cocoyl isethionate (56 g, 85% active) in water (237 mL), was added cocoyl glycine (60 g) and the resulting mixture was heated to 80° C. for 15 minutes. To this mixture at 80° C., 1,3-propane diol distearate (200 g) was added and stirred for additional 30 minutes. The resultant emulsion was then slowly cooled to 45° C. over two hours with gentle stirring. To this dispersion, water (78 mL) was added and mass was cooled to room temperature under gentle stirring over a period of two hours. pH was adjusted to 6 to 7 using citric acid. It was preserved with a 1.2% blend comprising 2-phenoxy ethanol, capryloyl glycine and undecylenoyl glycine in the ratio of (8:1:1)

Analysis:

Solids content: 42.7%

Viscosity at 25° C. Brookfield LV 4, rpm 12: 10000 cps pH (10% dispersion): 6.4

Sodium chloride content: 2%

Example 3

Preparation of Cold-Dispersible Pearlizing Blend Using 'Super-Mild' Surfactants in 1:1 Ratio: Sodium Cocoyl Glycinate:Sodium Cocoyl Isethionate 1:1 and 1,3-Propanediol Distearate

| Ingredients | Qty (g) |
|---|---|
| Sodium cocoyl glycinate (30% aq. Solution) | 262 |
| Sodium cocoyl isethionate (85% active) | 74 |
| Cocoyl glycine | 30 |
| 1,3-Propane diol distearate | 200 |
| Water | 422 |
| Citric acid | pH adjustment (6-7) |
| Preservative:Galguard NK 4 (2-phenoxy ethanol, capryloyl glycine and undecylenoyl glycine in the ratio of (8:1:1) | 12 |
| Weight of total batch | 1000 |

To a stirred solution of sodium cocoyl glycinate (262 g of 30% aqueous solution, 24% active with 5% sodium chloride) and sodium cocoyl isethionate (74 g, 85% active) in water (264 mL), was added cocoyl glycine (30 g) and the resulting mixture was heated to 80° C. for 15 minutes. To this mixture at 80° C., 1,3-propane diol distearate (200 g) was added and stirred for additional 30 minutes. The resultant emulsion was then slowly cooled to 45° C. over two hours with gentle stirring. To this dispersion, water (158 mL) was added and mass was cooled to room temperature under gentle stirring over a period of two hours. pH was adjusted to 6 to 7 using citric acid. It was preserved with a 1.2% blend comprising 2-phenoxy ethanol, capryloyl glycine and undecylenoyl glycine in the ratio of (8:1:1).

Analysis:
Solids content: 38.3%
Viscosity at 25° C. Brookfield LV 4, rpm 12: 5000 cps
pH (10% dispersion): 6.9
Sodium chloride content: 1.5%

Example 4

'Sulfate Free' Shampoo

| Ingredients | % (w/w) |
|---|---|
| Phase A | |
| Deionized water | To make 100.0 |
| Polyquaternium 10 | 0.2 |
| PEG-120 Methyl Glucose Trioleate (&) Propanediol (Glucamate VLT) | 4 |
| Phase B | |
| Sodium lauroyl glycinate (24%) | 28 |
| Sodium cocoyl taurate (40%) | 22 |
| Cocoamidopropyl betaine (29%) | 5 |
| Phase C | |
| Amodimethicone | 2 |
| Polyquaternium 7 | 2 |
| Pearlescent concentrate of Example 1 | 5 |
| EDTA Na$_2$ salt | 0.1 |
| Phenoxy ethanol, capryloyl glycine, and undecylenoyl glycine (8:1:1) | 1 |

Polyquaternium 10 and Glucamate VLT are dispersed in water separately to obtain phase A. Added phase B to phase A and mixed the mass until homogeneous. Added phase C and stirred until uniform mass is obtained. The pH of the final formulation was adjusted to 5.8-6.0 with 50% citric acid solution in water. The mass was blended with fragrance and color.

Example 5

'Sulfate-Free' Body Wash

| Ingredients | % (w/w) |
|---|---|
| Phase A | |
| Deionized water | To make 100.0 |
| Acrylate copolymer (Aqua SF-1) | 3 |
| Phase B | |
| Sodium cocoyl glycinate (30%) | 10 |
| Alkyl polyglucoside (C8/C10) | 10 |
| Sodium cocoyl taurate (40%) | 15 |
| Cocamidopropyl betaine (29%) | 5 |
| Phase C | |
| Dimethicone | 2 |
| Polyquaternium-7 | 2 |
| Hydrolyzed wheat protein | 1 |
| Pearlescent concentrate of Example 1 | 4 |
| EDTA disodium salt | 0.1 |
| Phenoxy ethanol, capryloyl glycine, and undecylenoyl glycine (8:1:1) | 1 |

Acrylate copolymer (Aqua SF 1) was dispersed in water to obtain phase A. The phase A was added to Phase B and mixed the mass until homogeneous. Finally phase C was added and stirred until uniform. The pH of the final formulation was adjusted with 50% citric acid aqueous solution. Finally the mass was blended with fragrance and color.

Example 6

Mild Face Wash

| Ingredients | % (w/w) |
|---|---|
| Phase A | |
| Deionized water | To make 100.0 |
| Hydroxy ethyl cellulose | 1.00 |
| Phase B | |
| Disodium laureth sulfosuccinate | 15.00 |
| Cocamidopropyl betaine | 15.00 |
| Sodium lauroyl sarcosinate | 10.00 |
| PEG-7 glyceryl cocoate glycerin | 2% |
| Glycerin | 5.00 |
| Phase C | |
| Hydrolyzed barley protein | 01.00 |
| Pearlescent concentrate of Example 1 | 05.00 |
| EDTA disodium salt | 00.10 |
| Phenoxy ethanol, capryloyl glycine, and undecylenoyl glycine (8:1:1) | 01.00 |

Hydroxyethyl cellulose was dispersed in water to obtain Phase A. Added phase B & C to phase A, stirred until uniform mass obtained. The pH of the final formulation was adjusted with 50% citric acid to 5.8-5.9 and blended with fragrance and color.

We claim:
1. A free flowing cold-dispersible, aqueous pearlizing concentrate comprising;
   a) 10 to 20% by weight of a mixture of an O-acyl isethionate (Formula III) and an N-acyl amino acid surfactant (Formula IV);

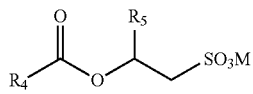
Formula III

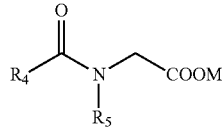
Formula IV wherein $R_4$ is selected from the group consisting of $C_7$ to $C_{21}$ saturated or unsaturated alkyl groups, $R_5$ is H or methyl and M is a cation selected from $Na^+$, $K^+$, and $NH_4^+$;
   b) 15 to 30% by weight of pearlizing wax selected from 1,3 propane diol esters of fatty acids (Formula V);

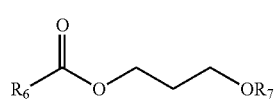
Formula V wherein $R_6$ is selected from the group consisting of $C_{13}$ to $C_{21}$ saturated or unsaturated alkyl groups, and $R_7$ is H or $R_6CO$;
   c) 2 to 6% by weight of N-acyl glycine (Formula VI);

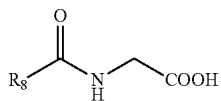
Formula VI wherein $R_8$ is selected from the group consisting of $C_7$ to $C_{21}$ saturated or unsaturated alkyl groups; and
   d) 0.8 to 1.2% by weight of a preservative system consisting of phenoxy ethanol, capryloyl glycine and undecylenoyl glycine.

2. The pearlescent aqueous concentrate according to claim 1, comprising a mixture of said O-acyl isethionate and said N-acyl amino acid surfactant, wherein the weight ratio of said O-acyl isethionate and said N-acyl amino acid surfactant is from 2.0:0.5 to 0.5:2.0.

3. The free flowing, aqueous, cold-dispersible pearlizing aqueous concentrate according to claim 1 which comprises;
   a) a mixture of sodium N-cocoyl glycinate and sodium cocoyl isethionate in the weight ratio of 2:1 in an amount of 10% w/w;
   b) 1,3-propane diol distearate in an amount of 20% w/w;
   c) cocoyl glycine in an amount of 5% w/w; and
   d) said preservative blend system consisting of phenoxy ethanol, capryloyl glycine, undecylenoyl glycine in the weight ratio of 8:1:1 in an amount of 1.2% w/w.

4. A Process for preparing a free flowing, aqueous, cold-dispersible pearlizing concentrate comprising:
   (i) Emulsifying a wax of Formula V by intimately mixing said wax of Formula V with 'super mild' a mixture of an O-acyl isethionate of Formula III and an N-acyl amino acid surfactant of Formula IV; and b) a non-ionic surfactant of Formula VI, in water at 75 to 80° C. to produce an emulsified mass;

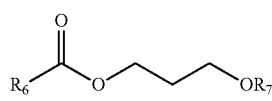
Formula V

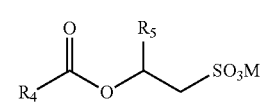
Formula III

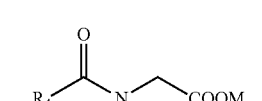
Formula IV

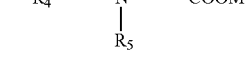
Formula VI (ii) Cooling the emulsified mass to 45° C. over 2 to 4 hours under gentle agitation;
   (iii) Adding a preservative system consisting of phenoxy ethanol, capryloyl glycine, and undecylenoyl glycine to the cooled mass to produce a concentrate;
   (iv) Holding the concentrate prepared in step (iii) at 45° C.-50° C. for 12-24 hours; and
   (v) Cooling the concentrate to room temperature.

5. The process of claim 4, further comprising adjusting the pH of the concentrate to between 6.0 and 7.0 using citric acid.

6. The aqueous pearlescent concentrate according to claim 1, wherein the aqueous concentrate has a solids content of at least 35% by weight.

7. The aqueous pearlescent concentrate according to claim 1, wherein the aqueous concentrate has a viscosity of between 3,000 and 20,000 cps.

8. The aqueous pearlescent concentrate according to claim 1, wherein the aqueous concentrate has a $D_{50}$ particle size of 5-15 μm.

9. A personal care composition comprising about 2 to 10% by weight of an aqueous concentrate according to claim 1.

* * * * *